United States Patent
Wang et al.

(10) Patent No.: US 9,507,488 B2
(45) Date of Patent: Nov. 29, 2016

(54) DISPLAY DEVICE, IMAGE DISPLAYING METHOD AND COMPUTERIZED TOMOGRAPHY APPARATUS

(71) Applicant: GE Medical Systems Global Technology Company, LLC, Waukesha, WI (US)

(72) Inventors: Xueli Wang, Beijing (CN); Zhenhua Xu, Beijing (CN); XiaoYan Yu, Beijing (CN)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 31 days.

(21) Appl. No.: 14/574,511

(22) Filed: Dec. 18, 2014

(65) Prior Publication Data

US 2015/0178954 A1 Jun. 25, 2015

(30) Foreign Application Priority Data

Dec. 20, 2013 (CN) .......................... 2013 1 0712898

(51) Int. Cl.
| | |
|---|---|
| *G06T 11/00* | (2006.01) |
| *G06T 11/60* | (2006.01) |
| *G09G 5/10* | (2006.01) |
| *G06F 3/0481* | (2013.01) |
| *G06T 7/00* | (2006.01) |
| *A61B 6/03* | (2006.01) |
| *A61B 6/00* | (2006.01) |

(52) U.S. Cl.
CPC ............ *G06F 3/0481* (2013.01); *A61B 6/032* (2013.01); *A61B 6/463* (2013.01); *G06T 11/008* (2013.01); *G06T 11/60* (2013.01); *G09G 5/10* (2013.01); *G09G 2320/0606* (2013.01); *G09G 2320/0686* (2013.01); *G09G 2380/08* (2013.01)

(58) Field of Classification Search
CPC combination set(s) only.
See application file for complete search history.

(56) References Cited

U.S. PATENT DOCUMENTS

| | | | | |
|---|---|---|---|---|
| 5,465,718 A | * | 11/1995 | Hochman | A61B 5/0059 348/164 |
| 5,699,798 A | * | 12/1997 | Hochman | A61B 5/0059 348/164 |
| 5,812,629 A | * | 9/1998 | Clauser | A61B 6/032 378/37 |
| 6,579,239 B1 | * | 6/2003 | Avinash | G01S 7/52073 600/443 |
| 6,671,540 B1 | * | 12/2003 | Hochman | A61B 5/0059 600/431 |
| 7,062,714 B1 | * | 6/2006 | Mo | A61B 8/461 358/474 |
| 7,853,063 B2 | | 12/2010 | Barski et al. | |
| 7,869,637 B2 | | 1/2011 | Baumgart et al. | |
| 2003/0236458 A1 | * | 12/2003 | Hochman | A61B 5/0059 600/431 |
| 2006/0067587 A1 | | 3/2006 | Sakai | |
| 2007/0173720 A1 | * | 7/2007 | Burdette | G01S 7/52071 600/438 |
| 2008/0050000 A1 | * | 2/2008 | Blaffert | G06T 7/0012 382/131 |
| 2009/0226063 A1 | * | 9/2009 | Rangwala | G06T 7/0012 382/128 |
| 2010/0141673 A1 | | 6/2010 | Gerade et al. | |
| 2012/0275668 A1 | * | 11/2012 | Chou | A61B 5/7405 382/118 |
| 2013/0051680 A1 | * | 2/2013 | Kono | G06T 7/0081 382/195 |

FOREIGN PATENT DOCUMENTS

WO 2012085163 A1 6/2012

* cited by examiner

*Primary Examiner* — Wesner Sajous
(74) *Attorney, Agent, or Firm* — GE Global Patent Operation

(57) ABSTRACT

A solid state power controller for an aircraft, the solid state power controller includes a solid state switching device for activating an electrical power output bus, a control unit for controlling the solid state switching device, and a current sensing circuit for monitoring current flowing in the electrical power output bus. The current sensing circuit includes a sensing fuse that provides a simplified and more reliable solid state power controller.

14 Claims, 4 Drawing Sheets

DISPLAY DEVICE, IMAGE DISPLAYING METHOD AND COMPUTERIZED TOMOGRAPHY APPARATUS

TECHNICAL FIELD

Embodiments of the present invention relate to the field of medical imaging diagnosis, more specifically, relate to a display device, an image display method and a Computerized Tomography (CT) apparatus.

BACKGROUND OF THE INVENTION

The computerized tomography (CT) apparatus generally comprises a scan device and a display device. The scan device scans an object to be diagnosed by emitting X-rays to the object to be diagnosed and receiving X-rays penetrating the object to be diagnosed, so as to obtain a scanning image that reflects the degree of absorption of X-rays by each site of the object to be diagnosed. The scan device further provides the obtained scanning image to the display device which displays the scanning image. Hence, an operator (e.g., a doctor) can observe the scanning image displayed by the display device, and determine whether there exists a lesion site in the scanning image.

The scanning image comprises a plurality of pixels, each pixel having gray scale corresponding to CT value, wherein the CT value represents the degree of absorption of X-rays by the site of the object to be diagnosed to which the pixel corresponds. Typically, the higher CT value represents a higher degree of absorption of X-rays, and the lower CT value represents a lower degree of absorption of X-rays. For example, the CT value of pixel corresponding to bone tissue is set to be +1000 Hu, the CT value of pixel corresponding to water 0 Hu, the CT value of pixel corresponding to air −1000 Hu, etc.

The CT value of pixel can be converted to a gray scale of pixel by setting an appropriate window width (WW) and window level (WL). The window width is a CT value range of pixels that will be displayed by different gray scales, i.e., pixels within the CT value range are displayed by different gray scales, the pixel with the CT value higher than this range is displayed as the maximum gray scale value, and the pixel with the CT value lower than this range is displayed as the minimum gray scale value. The window level is the central position of the window. For example, when the window width is 100 Hu and the window level is 0 Hu, the CT value range of pixels that will be displayed by different gray scales −50 Hu~+50 Hu.

In order to determine whether there exists a lesion site in the scanning image, the operator (e.g., doctor) may need to frequently and manually input new window width and/or window level to change the gray scale of pixel of the scanning image, so as to repetitively compare the differences between the scanning image that is initially displayed on the display device according to the initial window width and window level and the new scanning image that is displayed on the display device according to the new window width and/or window level, until it is determined whether there exists a lesion site in the scanning image.

In addition, when determining whether there exists a lesion site in the scanning image, the operator (e.g., doctor) may need to locally change the gray scale of pixel of the scanning image, e.g., changing the gray scale of pixel in the region of interest (ROI), so as to compare the region having the gray scale changed with other regions adjacent to it. However, since the scanning image wholly changes the gray scale of pixel according to the new window width and/or window level input by the operator (e.g., doctor), such need cannot be satisfied.

Therefore, a display device, which can simplify operations and enhance diagnosis reliability upon diagnosis, is needed.

BRIEF SUMMARY OF THE INVENTION

The objective of the illustrative embodiments of the present invention is to overcome the above and/or other problems in the prior art. Hence, the illustrative embodiments of the present invention provide a display device, an image display method and a computerized tomography (CT) apparatus which can simplify operations and enhance diagnosis reliability upon diagnosis.

According to an illustrative embodiment, a display device is provided, the display device comprises: a display unit, configured to display an image based on an image signal provided from the outside; a region of interest setting unit, configured to set a region of interest in the image displayed by the display unit; a gray scale changing unit, configured to change gray scale of pixel in the region of interest.

According to another illustrative embodiment, an image display method is provided, the method comprising: displaying an image based on an image signal provided from outside; setting a region of interest in the image as displayed; changing gray scale of pixel in the region of interest.

According to a further illustrative embodiment, a computerized tomography (CT) apparatus is provided, the CT apparatus comprising: a scan device, configured to scan an object to be diagnosed, so as to obtain an image signal of the object to be diagnosed; the display device as stated above, configured to receive the image signal from the scan device, and to display a scanning image of the object to be diagnosed.

Other features and aspects will become much clearer through the following detailed depictions, drawings and claims.

BRIEF DESCRIPTION OF THE DRAWINGS

The present invention can be better understood by depicting the illustrative embodiments of the present invention in combination with the following drawings.

DETAILED DESCRIPTION OF THE INVENTION

The specific embodiments of the present invention will be depicted below; it should be indicated that, during the process of specifically depicting these embodiments, in order to make a concise depiction, it is impossible for the present description to make detailed depiction to all features of the actual embodiments. It should be understood that, during the actual implementing process of any one embodiment, e.g., during the process of any one engineering project or designing project, in order to realize specific objectives of developers, and to meet system related or commerce related limits, usually various specific decisions will be made, such that a transition from one embodiment to another embodiment will also occur. In addition, it should also be understood that, although efforts as made during the developing process may be complicated and lengthy, for ordinary persons skilled in the art who are related with the contents disclosed by the present invention, some changes in design, manufacture or production on the basis of the technical contents disclosed by the present invention are only customary technical means, and should not be construed as the contents of the present invention being insufficiently disclosed.

Unless defined otherwise, the technical terms or scientific terms that are used in the claims and the description should have general meanings as understood by persons with ordinary skills in the technical field to which the present invention belongs. Such words as "first", "second" used in the description and claims of the present invention patent application do not denote any sequence, quantity or significance, and are only used to distinguish different constituting parts. Such words as "one" only represent that at least one exists, without denoting quantity limitation. Such words as "including" or "comprising" mean that the elements or objects appearing before the words "including" or "comprising" cover the elements or objects and equivalent elements listed after the words "including" or "comprising", not excluding other elements or objects. Such words as "connection" or "link" are not limited to physical or mechanical connection, and are not limited to direct or indirect connections, neither.

Figure 1:
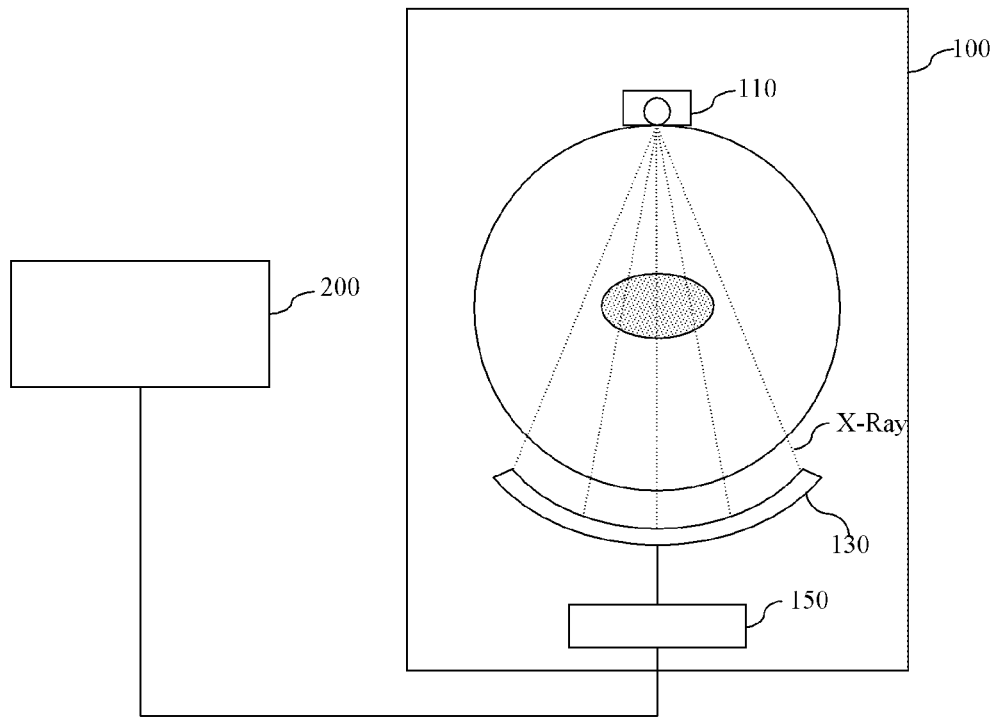
FIG. 1 provides a schematic block diagram of a Computerized Tomography (CT) apparatus according to an illustrative embodiment.
Figure 2:
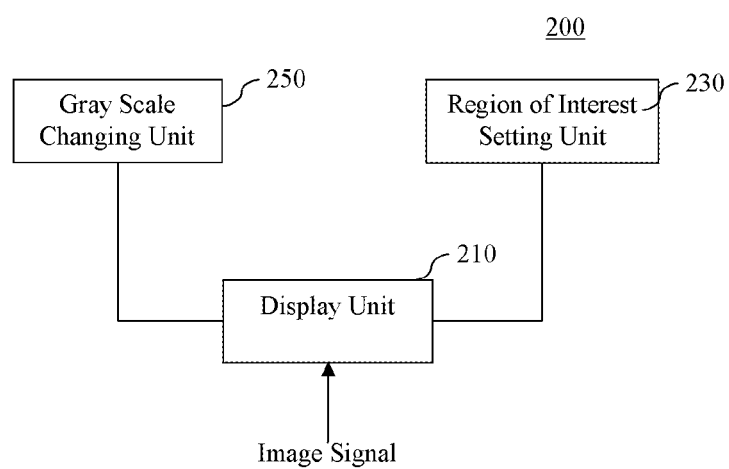
FIG. 2 provides a schematic block diagram of a display device according to an illustrative embodiment.

FIG. 1 provides a schematic block diagram of a Computerized Tomography (CT) apparatus according to an illustrative embodiment; FIG. 2 provides a schematic block diagram of a display device according to an illustrative embodiment. As shown in FIG. 1 and FIG. 2, the CT apparatus can comprise a scan device 100 and a display device 200.

The scan device 100 can scan an object to be diagnosed. For example, the scan device 100 can comprise an X-ray generating means 110, an X-ray receiving means 130 and an image processing means 150. The X-ray generating means 110 can generate X-rays, and can emit the generated X-rays to the object to be diagnosed. The X-ray receiving means 130 can receive the X-rays that penetrates the object to be diagnosed, and can convert the received X-rays into electrical signals. The image processing means 150 can process the electrical signals that are converted by the X-ray receiving means 130, so as to generate image signals. In addition, the image processing means 150 can provide the generated image signals to the display device 200.

As shown in FIG. 2, the display device 200 can comprise a display unit 210, a region of interest setting unit 230 and a gray scale changing unit 250. The display unit 210 can display the scanning image of the object to be diagnosed based on image signals provided by the scan device 100 (i.e., the image processing means 150). As such, the operator (e.g., doctor) can observe the scanning image displayed on the display unit 210.

Figure 3:
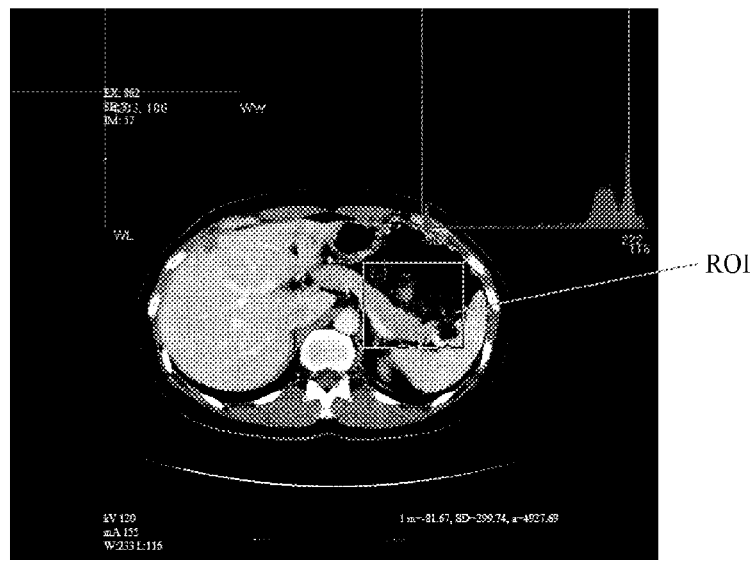
FIG. 3 shows a scanning image displayed by the display device according to an illustrative embodiment.

The region of interest setting unit 230 can set a region of interest (ROI) in the image displayed by the display unit 210. For example, the region of interest setting unit 230 can comprise input means such as keyboard, mouse, and touch screen, and the operator can set or select ROI in the scanning image displayed on the screen of the display unit 210 via such input means. FIG. 3 shows a scanning image displayed by the display device according to an illustrative embodiment. As shown in FIG. 3, the ROI marked by the operator can be in the shape of rectangle. However, the illustrative embodiment is not limited to such situation. The ROI can also be various shapes, such as roundness, ellipse, polygon, etc. In addition, firstly, a region in the scanning image corresponding to a tissue or organ of the object to be diagnosed can be automatically identified through a region growing algorithm utilizing the relation between the CT value of pixel and the CT value of adjacent pixel of the scanning image; then, the operator can set the identified region corresponding to the tissue or organ to be ROI. Here, the region growing algorithm can be a method of aggregating pixels or sub-regions into a bigger region according to the predefined rules. For example, the region growing algorithm can take a pixel or a group of pixels as a seed, and attach adjacent pixels similar to the properties (a specific range of gray scale or color) of the seed to the seed of the growing region.

The gray scale changing unit 250 can change gray scale of pixel in the ROI. For example, the gray scale changing unit 250 can change gray scale of pixel in the ROI by changing window width and/or window level for determining gray scale of pixel in the ROI.

In an illustrative embodiment, the gray scale changing unit 250 can firstly determine initial window level and initial window width of the ROI based on CT value of pixel in the ROI. The initial window level and initial window width of the ROI can be same to or different from the initial window level and initial window width of the whole scanning image. When the initial window level and initial window width of the ROI are different from the initial window level and initial window width of the whole scanning image, the gray scale changing unit 250 can determine gray scale of pixel in the ROI based on the initial window level and initial window width of the ROI. Now, the display unit 210 can display a scanning image comprising the ROI having pixels with the gray scale that is determined based on the initial window level and initial window width of the ROI. In other words, the display unit 210 can display a scanning image in which local gray scale is changed. As shown in FIG. 3, the initial window level of the ROI region can be 106, and the initial window width can be 233.

Then, the gray scale changing unit 250 can continuously change the window level of the ROI starting from the initial window level and/or continuously change the window width of the ROI starting from the initial window width, thereby changing gray scale of pixel in the ROI. Meanwhile, the display unit 210 can real time display a scanning image in which local gray scale is changed.

Figure 4:
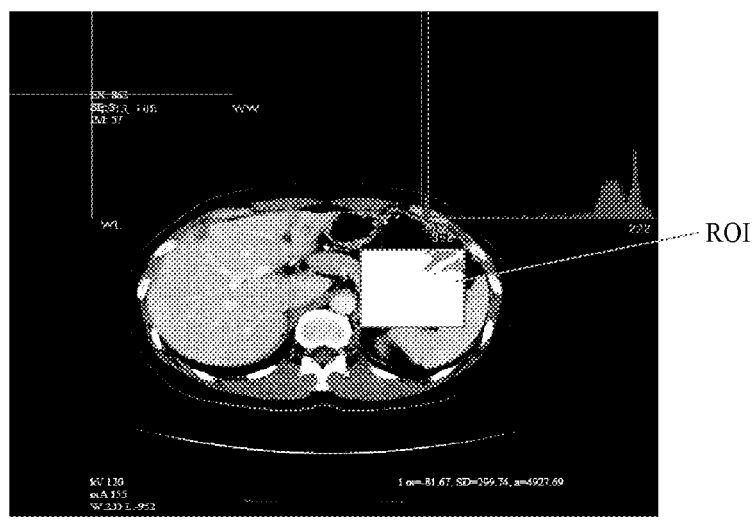
FIGS. 4, 5, and 6 show scanning images displayed by the display device and comprising the region of interest with gray scale of pixel changed according to illustrative embodiments.
Figure 5:
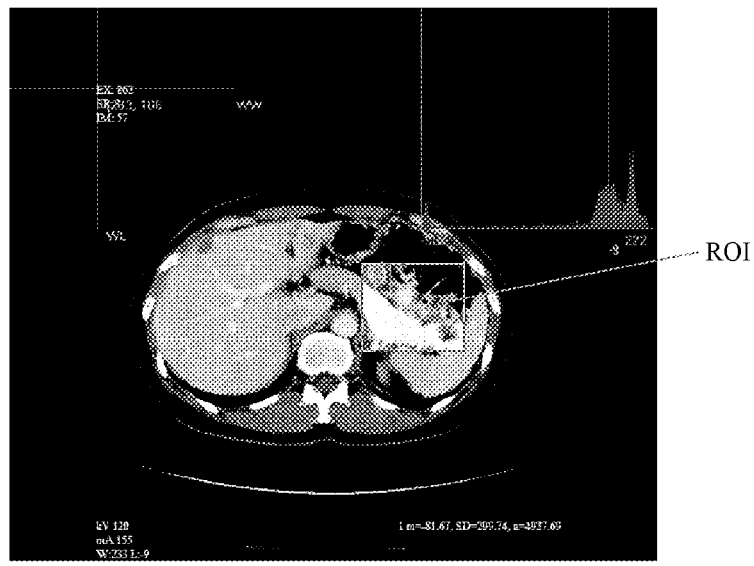
Figure 6:
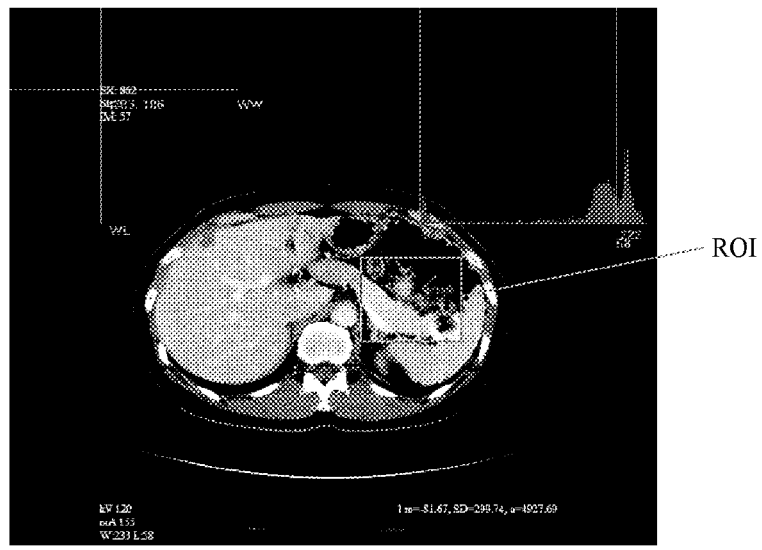

FIGS. 4-6 show scanning images displayed by the display device and comprising the region of interest with gray scale of pixel changed according to illustrative embodiments. In the scanning image with local gray scale changed as shown in FIG. 4, the window level of the ROI region can be −952, and the window width can be 233. In the scanning image with local gray scale changed as shown in FIG. 5, the window level of the ROI region can be −9, and the window width can be 233. In the scanning image with local gray scale changed as shown in FIG. 6, the window level of the ROI region can be 58, and the window width can be 233.

Thus, the operator (e.g., doctor) can change the window level and/or window width of the ROI so as to compare the ROIs comprising pixels having gray scales that are determined according to different window levels and/or window widths, and/or can change the window level and/or window width of the ROI region and keep the window levels and window widths of other regions rather than the ROI region in the scanning image unchanged so as to compare the ROI having pixels of gray scales that are determined according to different window levels and/or window widths and the regions adjacent to the ROI region, thereby determining whether there exists a lesion in the ROI region.

Figure 7:
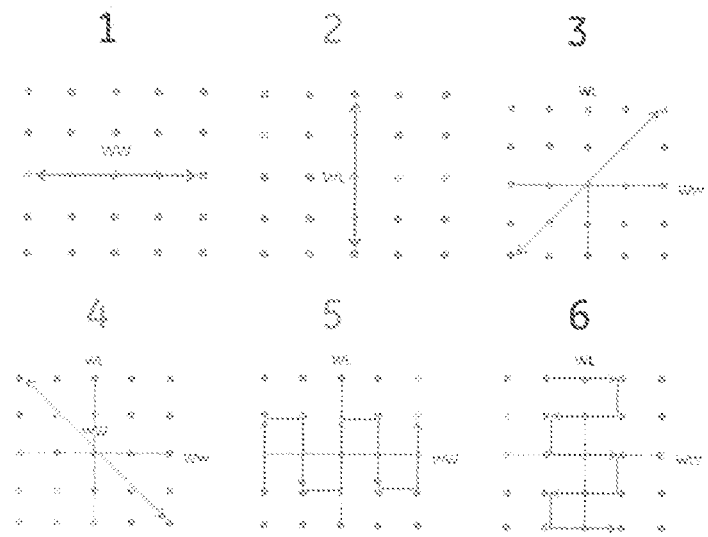
FIG. 7 shows various alternative manners of changing gray scale of pixel in the region of interest according to an illustrative embodiment.

According to an illustrative embodiment, the gray scale changing unit 250 can change the gray scale of pixel in the ROI region pursuant to various manners. FIG. 7 shows various alternative manners of changing gray scale of pixel in the region of interest according to an illustrative embodiment. For example, while keeping the window level of the ROI as the initial window level, the gray scale changing unit 250 can continuously change the window width (WW) of the ROI starting from the initial window width, as shown in (1) of FIG. 7; while keeping the window width of the ROI as the initial window width, it can continuously change the window level (WL) of the ROI starting from the initial window level, as shown in (2) of FIG. 7; it can concurrently and continuously change the window level of the ROI and the window width of the ROI starting from the initial window level and initial window width, as shown in (3) of FIG. 7 and (4) of FIG. 7.

In addition, as shown in (5) of FIG. 7 and (6) of FIG. 7, the gray scale changing unit 250 can change the gray scale of pixel in the ROI in the manner of vibration. That is, as shown in (5) of FIG. 7, the gray scale changing unit 250 can increase (or decrease) the window level of the ROI starting from the initial window level in the case of keeping the initial window width unchanged. Then, the gray scale changing unit 250 can increase (or decrease) the window width of the ROI starting from the initial window width in the case of keeping the current window level unchanged. Next, the gray scale changing unit 250 can increase (or decrease) the window level of the ROI starting from the current window level in the case of keeping the current window width unchanged. Then, the gray scale changing unit 250 can repeat the above operations, so as to change the window level and window width of the ROI in the manner of vibration, such that the gray scale of pixel in the ROI is changed in the manner of vibration. As shown in (6) of FIG. 7, the gray scale changing unit 250 can increase (or decrease) the window width of the ROI starting from the initial window width in the case of keeping the initial window level unchanged. Then, the gray scale changing unit 250 can increase (or decrease) the window level of the ROI starting from the initial window level in the case of keeping the current window width unchanged. Next, the gray scale changing unit 250 can increase (or decrease) the window width of the ROI starting from the current window width in the case of keeping the current window level unchanged. Then, the gray scale changing unit 250 can repeat the above operations, so as to change the window level and window width of the ROI in the manner of vibration, such that the gray scale of pixel in the ROI is changed in the manner of vibration. However, the illustrative embodiments are not limited to the above situations; the gray scale changing unit 250 can change the gray scale of pixel in the ROI pursuant to various manners preset by manufactures or selected by operators.

In addition, in order to be convenient for observation and comparison by the operator (e.g., doctor), the gray scale changing unit 250 can repetitively change the gray scale of pixel in the ROI. That is, after continuously changing the pixel from the first gray scale to the second gray scale according to the first manner, the gray scale changing unit 250 can continuously change the pixel from the second gray scale to the first gray scale according to the manner opposite to the above first manner. In other words, the gray scale changing unit 250 can repetitively perform the first gray scale changing operation and the second gray scale changing operation; during the first gray scale changing operation, the gray scale changing unit 250 can change the gray scale of pixel in the ROI according to the first manner; during the second gray scale changing operation, the gray scale changing unit 250 can change the gray scale of pixel in the ROI according to the second manner opposite to the first manner. Hence, the operator (e.g., doctor) can diagnose whether there exists a lesion in the ROI when the gray scale of pixel in the ROI undergoes repetitive changes.

Figure 8:
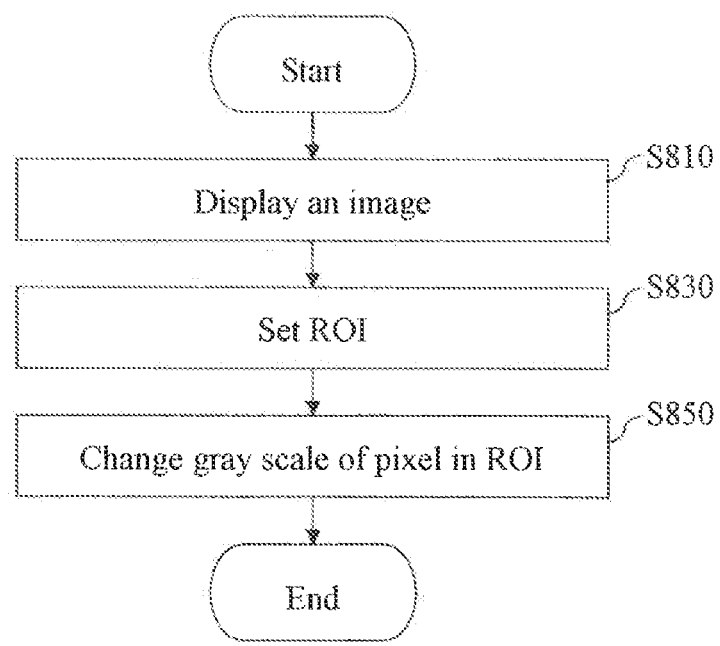
FIG. 8 provides a flow chart for an image display method according to an illustrative embodiment.

FIG. 8 provides a flow chart for an image display method according to an illustrative embodiment. For the sake of conciseness, the depiction of elements and features same or similar to the elements and features as described above will be omitted.

As shown in FIG. 8, firstly, an image can be displayed (S810) based on an image signal provided from the outside (e.g., the scan device 100 as shown in FIG. 1). Here, the image can be a scanning image that is obtained by conducting computerized tomography scanning to the object to be diagnosed, as shown in FIG. 3.

Then, in Step S830, a region of interest (ROI) can be set in the displayed image. The ROI can be set manually or automatically. For example, a region corresponding to a tissue or organ of the object to be diagnosed in the displayed image can be identified, and the identified region corresponding to the tissue or organ can be set as a region of interest.

After the ROI is set, gray scale of pixel in the ROI can be changed (S850). For example, the initial window level and window width of the ROI can be determined based on CT value of pixel in the ROI. Then, the gray scale of pixel in the ROI can be changed by continuously changing window level of the region of interest starting from the initial window level and/or continuously changing window width of the region of interest starting from the initial window width. Here, the gray scale of pixel in the ROI can be determined based on the window width and window level of the ROI. For example, the gray scale of pixel in the ROI can be changed according to various anticipated manners such as the manners as described above with reference to (1) to (6) in FIG. 7. In addition, the gray scale of pixel in the ROI can also be repetitively changed.

Meanwhile, while the gray scale of pixel in the ROI is changed, the image comprising the ROI with the gray scale of pixel changed can be displayed. Therefore, the operator (e.g., doctor) can compare the ROIs comprising pixels having different gray scales that are determined according to different window levels and/or window widths, and/or can compare the ROI having pixels of gray scales and the regions adjacent to the ROI region that are determined according to different window levels and/or window widths, thereby determining whether there exists a lesion in the ROI region.

According to an illustrative embodiment, gray scales of local regions of a scanning image can be changed pursuant to preset or selected manners, such that the operator (e.g., doctor) can conveniently compare the local regions with different gray scales and/or compare the local regions and the regions adjacent to them, thereby determining whether there exists a lesion in the local regions. In addition, the gray scales of local regions of the scanning image can be changed automatically, so complicated operations of the operator are not needed. Hence, diagnostic procedures are simplified, diagnosis time is shortened, and diagnostic efficiency and reliability are improved.

Some illustrative embodiments have been depicted above. However, it can be understood that various amendments can be made. For example, if the technology as depicted is executed in a different order, and/or, if the assemblies in the system, framework, device or electric circuit as depicted are combined in a different manner and/or substituted or supplemented by additional assemblies or their equivalents, an appropriate result can be achieved. Accordingly, other embodiments all fall within the protection scopes of the claims.

What is claimed is:

1. A display device, comprising:
    a display unit configured to display an image based on an image signal received from a scan device;
    a region of interest setting unit configured to set a region of interest in the image displayed by the display unit; and
    a gray scale changing unit configured to change a gray scale of pixels in the region of interest comprising:
        determine an initial window level and an initial window width of the region of interest based on CT values of pixels in the region of interest, and
        change a gray scale of the pixels in the region of interest by at least one of: continuously changing a window level of the region of interest starting from the initial window level and continuously changing a window width of the region of interest starting from the initial window width.

2. The display device according to claim 1, wherein the image signal comprises a computerized tomography scan of an object.

3. The display device according to claim 2, wherein the region of interest setting unit is further configured to:
    identify a region corresponding to a at least one of: a tissue and an organ of the object, and
    set the region corresponding to the identified at least one of: a tissue and an organ as the region of interest.

4. The display device according to claim 1, wherein the gray scale changing unit is further configured to change gray scale of pixel in the region of interest according to at least one of:
    continuously changing the window width of the region of interest starting from the initial window width, in the case that the window level of the region of interest is maintained to be the initial window level,
    continuously changing the window level of the region of interest starting from the initial window level, in the case that the window width of the region of interest is maintained to be the initial window width, and
    concurrently and continuously changing the window level of the region of interest and the window width of the region of interest starting from the initial window level and the initial window width.

5. The display device according to claim 1, wherein the initial window level is a current window level of the region of interest and the initial window width is a current window width of the region of interest.

6. The display device according to claim 1, wherein the gray scale changing unit is further configured to repetitively change gray scale of pixel in the region of interest by repetitively performing a first gray scale changing operation and a second gray scale changing operation, wherein during the first gray scale changing operation, the gray scale changing unit changes gray scale of pixel in the region of interest according to a first manner, and during the second gray scale changing operation, the gray scale changing unit changes gray scale of pixel in the region of interest according to a second manner opposite to the first manner.

7. The display device according to claim 1, wherein the gray scale of pixels of the image in regions outside the region of interest is kept unchanged.

8. An image display method, the method comprising:
    displaying an image based on a computerized tomography image signal of an object;
    setting a region of interest in the image; and
    changing a gray scale of pixels in the region of interest comprising:
determining an initial window level and an initial window width of the region of interest based on CT values of pixels in the region of interest, and
    changing the gray scale of the pixels in the region of interest by at least one of: continuously changing a window level of the region of interest starting from the initial window level and continuously changing a window width of the region of interest starting from the initial window width.

9. The method according to claim 8, wherein setting a region of interest comprises:
    identifying a region corresponding to one of: a tissue and an organ of the object;
    setting the identified region corresponding to the one of: a tissue and an organ as the region of interest.

10. The method according to claim 8, wherein the gray scale of pixel in the region of interest is changed according to at least one of the following manners:
    continuously changing window width of the region of interest starting from the initial window width, in the case that window level of the region of interest is maintained to be the initial window level;
    continuously changing window level of the region of interest starting from the initial window level, in the case that window width of the region of interest is maintained to be the initial window width; and
    concurrently and continuously changing window level of the region of interest and window width of the region of interest starting from the initial window level and the initial window width.

11. The method according to claim 8, wherein
    the initial window level is a current window level of the region of interest and the initial current window width is a current window width of the region of interest.

12. The method according to claim 8, wherein changing gray scale comprises:
    repetitively changing gray scale of pixel in the region of interest by repetitively performing a first gray scale changing operation and a second gray scale changing operation, wherein during the first gray scale changing operation, the gray scale of pixels in the region of interest is changed according to a first manner, and during the second gray scale changing operation, the gray scale of pixels in the region of interest is changed according to a second manner opposite to the first manner.

13. The method according to claim 8, further comprising:
displaying the gray scale of pixels of the image in regions outside the region of interest unchanged.

14. A computerized tomography apparatus, comprising:
a scan device configured to scan an object to obtain an image signal of the object; and
a display device configured to receive the image signal from the scan device and display an image of the object based on the image signal, the display device comprising a display unit configured to display the image said image comprising a region of interest,
wherein the gray scale of pixels in the region of interest is changed by repetitively performing a first gray scale changing operation and a second gray scale changing operation, wherein during the first gray scale changing operation, the gray scale of pixels in the region of interest is changed according to a first manner, and during the second gray scale changing operation, the gray scale of pixels in the region of interest is changed according to a second manner opposite to the first manner.

* * * * *